United States Patent [19]
Adams et al.

[11] Patent Number: 6,156,494
[45] Date of Patent: Dec. 5, 2000

[54] SERIALLY DIRECTED COMBINATORIAL SYNTHESIS ON FIBER OPTIC ARRAYS

[75] Inventors: Christopher Adams, Somerville; T. Christian Boles, Waltham, both of Mass.; Coimbatore Nagaraja Sridhar, San Diego, Calif.

[73] Assignee: Mosaic Technologies, Boston, Mass.

[21] Appl. No.: 08/959,241

[22] Filed: Oct. 28, 1997

[51] Int. Cl.[7] .......................... C12Q 1/00; G01N 31/00; C07K 1/04; C07B 61/00
[52] U.S. Cl. .................. 435/4; 435/7.1; 436/8; 436/518; 530/333; 536/25.3; 536/25.31
[58] Field of Search ............... 436/518, 8; 435/7.1, 435/4, DIG. 49; 530/333; 336/25.3, 25.31

[56] References Cited

U.S. PATENT DOCUMENTS

| | | | |
|---|---|---|---|
| 5,143,854 | 9/1992 | Pirrung et al. | 436/518 |
| 5,565,324 | 10/1996 | Still et al. | 435/6 |
| 5,627,922 | 5/1997 | Kopelman | 385/12 |
| 5,646,285 | 7/1997 | Baindur et al. | 546/298 |
| 5,690,894 | 11/1997 | Pinkel | 422/68.1 |

OTHER PUBLICATIONS

Hensman, et al., "Total radiated power, infrared output, and heat generation by cold light sources at the distal end of endoscopes and fiber optic bundle of light cables," *Surg. Endosc.*, 12:335–337 (1998).

*Primary Examiner*—Bennett Celsa
*Assistant Examiner*—Joseph W. Ricigliano
*Attorney, Agent, or Firm*—Townsend and Townsend and Crew LLP

[57] ABSTRACT

A method has been developed which utilizes functionalized optical fibers as a solid support for the assembly of combinatorial libraries of compounds. The optical fibers are used to direct light, heat or a combination thereof to the compounds tethered to the fibers surface. Utilizing the method of the instant invention reactions occurring by both photochemically and thermally allowed pathways are accessible. In a preferred embodiment of the invention, the optical fibers are used to screen the array by fluorescence spectroscopy of labeled target molecules which bind to the immobilized library compounds.

37 Claims, 3 Drawing Sheets

SERIALLY DIRECTED COMBINATORIAL SYNTHESIS ON FIBER OPTIC ARRAYS

FIELD OF THE INVENTION

This invention relates to methods of synthesizing and screening combinatorial libraries of oligomeric and non-oligomeric organic compounds.

BACKGROUND OF THE INVENTION

The discovery of new compounds which exhibit an affinity for biological receptors holds the promise of providing agents which have useful bioactive properties. Biological receptors of interest include, for example, enzymes, antibodies, oligonucleotides, cell surface receptors, etc. A molecule which binds to a biological target can often be expected to display bioactive properties such as pharmacological, herbicidal or pesticidal activity. In the absence of a bioactive response, the affinity of an agent for a biological target is itself a useful property which can be used to probe, for example, the nature of enzymatic reactions, membrane transport of ions, cellular recognition, antibody activity, etc. Until quite recently, the discovery of useful bioactive molecules was either serendipitous or it occurred by the serial synthesis and screening of a large number of potentially active compounds.

The serial synthesis and screening of individual organic molecules which have a potential for pharmacological or other activity is a laborious and time-consuming task. The search for compounds with desirable biological properties begins with the identification of one or more lead compounds which bind to a biological target such as a receptor, a pathogen or an enzyme. To identify a lead compound, numerous compounds are synthesized in an effort to define structural features essential for the desired bioactivity. Once a lead compound has been identified, the structure of the lead compound is varied, in a somewhat orderly fashion, in an attempt to optimize its activity. In general, it is necessary to synthesize and evaluate many compounds in both the lead identification and the optimization steps. Each synthesized compound must be purified, characterized and screened for activity. Recent advances in combinatorial methods of synthesis have considerably simplified the drug discovery process and have improved the means by which large numbers of organic compounds can be synthesized and screened for activity.

Combinatorial synthesis is a high-throughput synthesis technique which has been used to rapidly produce and screen libraries of up to tens of thousands of compounds. A very wide range of chemistry types are amenable to library generation. For example, combinatorial methods have been used to synthesize libraries of oligomeric compounds such as, for example, peptides (Pirrung, et al., U.S. Pat. No. 5,143,854), peptoids (Simon, R. J., et al., *Proc. Natl. Acad. Sci. U.S.A.*, 91:11138–11142 (1994)), and oligodeoxynucleotides (Fodor, et al., PCT Publication No. WO 92/10092). Combinatorial methods have also been used to synthesize non-oligomeric compounds such as, for example, benzodiazepines (Bunin, et al., *J. Am. Chem. Soc.*, 114:10997–10998 (1992)), diketopiperazines (Gordon, D. W., et al., *BioMed. Chem. Lett.*, 5:47–50 (1995)) and pyrrolidines (Murphy, M. M., et al., *J. Am. Chem. Soc.*, 117:7029–7030 (1995)).

Combinatorial libraries have been synthesized both in solution and using solid supports. See, for example, Thomson, L. A., et al., *Chem. Rev.*, 96:555–600 (1996). The principal advantage of a solution-phase approach is that a method does not need to be developed to attach the initial starting material onto the support or to cleave the final product from the support. In spite of these advantages, the majority of the published work on combinatorial libraries has utilized solid-phase synthesis. This is largely due to the relative ease of purifying the support-bound compounds away from excess reagents.

The solid-phase assembly of combinatorial libraries relies on a solid support which bears on its surface a large number of reactive functional groups to which the first component ("building block") of the putative library is attached. The solid support and the attached building block are then contacted with a second building block and any reagent necessary to react the first and second building blocks. The excess second building block and the reagents are removed by washing the solid support with an appropriate solvent. These steps are repeated with additional building blocks and reagents until the library of desired compounds is assembled.

Solid supports made of a variety of materials have been used in assembling combinatorial libraries. A solid support can be manufactured of virtually any material which remains chemically inert and insoluble during the various reaction cycles required to assemble the library. Commonly used solid supports include polystyrene cross-linked with 1–2% divinylbenzene (Merrifield, R. B., *J. Am. Chem. Soc.*, 85:2149–2154 (1963)), aminomethylated polystyrene resin (Plunkett, M. J., et al., *J. Am. Chem. Soc.*, 117:3306–3307 (1995)) and amino-functionalized poly(ethylene glycol)-grafted polystyrene resin (Baldwin, J. J., et al., *J. Am. Chem. Soc.*, 117:5588–5589 (1995)).

Although methods exist in the art for the surface modification of both siliceous (e.g., glass, quartz, mica, etc.) and plastic surfaces with reactive functional groups, these various techniques have yet to be applied to the modification of optical fibers to allow their use as solid supports for combinatorial libraries. The use of optical fibers as solid supports has numerous advantages. The optical fiber can be used to deliver electromagnetic energy in the form of, for example, light, heat or a combination thereof to the reactants on the surface of the fiber. Further, spectroscopic data available via use of the functionalized optical fibers allows a combinatorial library of compounds to be screened for a desirable characteristic while the compounds remain bound to the optical fiber.

The use of optical fiber strands for medical, biochemical and chemical analytical determinations has undergone rapid development. The use of optical fibers for such purposes and techniques is described by Milanovich, et al., "Novel Optical Fiber Techniques for Medical Application", Proceedings of the SPIE 28th Annual International Technical Symposium on Optics and Electro-Optics, Vol. 494, 1980; Seitz, W. R., "Chemical Sensors Based on Immobilized Indicators and Fiber Optics", in C.R.C. Critical Reviews in Analytical Chemistry, Vol. 19, 1988, pp. 135–173; Wolfbeis, O. S., "Fiber Optical Fluorosensors in Analytical Chemistry", in MOLECULAR LUMINESCENCE SPECTROSCOPY, METHODS AND APPLICATIONS, Schulman, S. G., Ed., Wiley and Sons, New York. The optical fiber strands are typically glass or plastic extended rods having a small cross-sectional diameter. When light energy is projected into one end of the fiber strand, the angles at which the various light rays strike the surface are greater than the critical angle; and such rays are "piped" through the strand's length by successive internal reflections and eventually emerge from the opposite end of the strand. When the individual strands are bundled together, the collection is referred to as an "imaging fiber." An imaging fiber can comprise several thousand individual 3–4 μm-diameter optical fibers melted and drawn together in a coherent manner such that an image can be carried from one end to the other. See, for example, Chigusa, Y., et al., *Optoelectronics*, 1:203–216 (1986); Mogi, M., et al., *Proc. SPIE-Int. Soc. Opt. Eng.*, 1067:172–181 (1989). Typically, bundles of these strands are used collectively in a variety of different applications. One application of particular interest resides in the field of optical sensors.

For making an optical fiber into an optical sensor, one or more light absorbing fluorescent dyes are located at the distal end of the optical fiber. For example, Walt, et al. (U.S. Pat. No. 5,320,814) teaches optical sensors which comprise, at their distal ends, a polymeric substance of predetermined chemical composition and a dye compound which is disposed in admixture with the polymeric substance. The admixture is formed by the photopolymerization of an acryloyl derivative of a fluorescent dye. The admixed dye compound absorbs light energy and, in the presence of an analyte, generates a modified spectral response which is detected at the proximal tip of the fiber. Importantly, Walt, et al. neither teaches nor contemplates the assembly of an orderly combinatorial array of compounds using optical fibers as a solid synthesis support. Further, Walt, et al. neither teaches nor contemplates screening a combinatorial library of individual compounds, immobilized on an optical fiber, by using the fiber to spectroscopically detect interactions between the library compounds and a fluorescent-labeled analyte.

Methods of detecting optical changes at the distal tip of individual fibers of an optical imaging fiber are known in the art. One such means of detection utilizes an imaging fiber in association with an epifluorescence microscope and a charge-coupled device (CCD) camera. Bronk, K. S., et al., *Anal. Chem.*, 67:2750–2757 (1995). The apparatus described by Bronk, et al. allows for the simultaneous imaging and chemical sensing of a sample.

In spite of the recent advances in the use of optical fibers as chemical sensors, a method has yet to be produced for the use of optical fibers for the synthesis and screening of combinatorial libraries of compounds. Chemical synthesis of a compound library on an optical fiber would allow electromagnetic energy such as light and/or heat to be supplied to the reactants on the surface of the optical fiber. Application of these forms of energy to the reactants facilitates those reactions requiring the input of light or heat energy.

Combinatorial libraries can be assembled by functionalizing individual optical fibers arranged in an imaging fiber with a different component of the library. Following the assembly of the library, the library compounds can be screened for desirable properties such as their binding to, for example, a fluorescent labeled biomolecule. The screening for binding can be conducted while the compound is attached to the optical fiber and the binding can be detected using the optical fiber. Also, using the imaging properties of the imaging fiber, the individual fibers to which the fluorescent molecule has bound, can be easily located. Thus, a method utilizing optical fibers for the synthesis and screening of a combinatorial library of compounds would represent a significant addition to the growing arsenal of techniques for the synthesis and screening of these libraries. Quite surprisingly, the instant invention provides such a method.

SUMMARY OF THE INVENTION

Improved techniques for the synthesis and screening of combinatorial libraries, including those of oligomeric and small molecules, are provided by the present invention.

It has now been discovered that optical fibers can be used as a solid support for assembling combinatorial libraries of organic compounds. Thus, in one aspect, the invention provides a method of making an array of compounds on a substrate, the substrate comprising at least two regions, wherein each of the regions comprises an optical fiber which is functionalized with a reactive group, the method comprising:

(a) attaching a first component to the reactive group on the optical fiber of the first region and a first component to the reactive group on the optical fiber of the second region;

(b) delivering a first activator to the first component on the first optical fiber of the first region via the optical fiber of the first region;

(c) delivering a second component to the first component on the optical fiber of the first region;

(d) delivering a second activator to the first component on the optical fiber of the second region via the optical fiber of the second region;

(e) delivering a second component to the first component on the optical fiber of the second region.

In a second aspect, the invention provides for a method of performing intramolecular reactions on a fiber optic support. In this aspect, the invention provides a method of making an array of compounds on a substrate, the substrate comprising at least two regions, wherein each of the regions comprises an optical fiber which is functionalized with a reactive group, the method comprising:

(a) attaching a first component to the reactive group on the optical fiber of the first region and a first component to the reactive group on the optical fiber of the second region; and (b) delivering a first activator to the first component on the optical fiber of the first region via the optical fiber of the first region and a second activator to the first component on the optical fiber of the second region via the optical fiber of the second region.

DETAILED DESCRIPTION OF THE INVENTION AND PREFERRED EMBODIMENTS

Definitions

As used herein, the term "activator" refers to electromagnetic energy, heat and combinations.

"Region" as used herein refers to at least one optical fiber. When a region comprises more than one optical fiber, the optical fibers can be arranged in a contiguous or adjacent manner or the fibers of the region can be discontinuous in their arrangement.

In spite of the recent advances in the use of optical fibers as chemical sensors, prior to the instant invention, a method had not been produced for the use of optical fibers for the synthesis and screening of combinatorial libraries of compounds. Chemical synthesis of a compound library on an optical fiber allows light and/or heat to be supplied to the reactants on the surface of the optical fiber. Application of these forms of energy to the reactants facilitates those reactions requiring the input of light or heat energy. Individual optical fibers arranged in an imaging fiber can each be functionalized with a different component of the library. The binding of the compounds on the individual fibers to, for example, a fluorescent labeled biomolecule can be detected using the optical fiber. Also, using the imaging properties of the imaging fiber, the individual fibers to which the fluorescent molecule has bound, can be easily located.

Thus, in one aspect, the invention provides a method of making an array of compounds on a substrate, the substrate comprising at least two regions, wherein each of the regions comprises an optical fiber which is functionalized with a reactive group, the method comprising:

(a) attaching a first component to the reactive group on the optical fiber of the first region and a first component to the reactive group on the optical fiber of the second region;

(b) delivering a first activator to the first component on the first optical fiber of the first region via the optical fiber of the first region;

(c) delivering a second component to the first component on the optical fiber of the first region;

(d) delivering a second activator to the first component on the optical fiber of the second region via the optical fiber of the second region;

(e) delivering a second component to the first component on the optical fiber of the second region.

In embodiments wherein regions comprise more than one optical fiber, the first region comprises at least 10 optical fibers. In a preferred embodiment, the first region comprises at least 50 optical fibers and more preferably at least 100 optical fibers. In a still more preferred embodiment, the first region comprises at least 1,000 optical fibers.

In certain embodiments, the optical fibers of the first region are arranged in a contiguous or adjacent manner. In another embodiment, the optical fibers of the first region are arranged in a non-contiguous or non-adjacent manner. In each of these embodiments, the optical fibers of the second region are arranged in contiguous or adjacent manner, or a non-contiguous or non-adjacent manner. The invention encompasses within its scope arranging the optical fibers of each region in the same manner or different manner as the region immediately preceding or succeeding it.

In a second aspect, the invention provides for a method of performing intramolecular reactions on a fiber optic support. In this aspect, the invention provides A method of making an array of compounds on a substrate, the substrate comprising at least two regions, wherein each of the regions comprises an optical fiber which is functionalized with a reactive group, the method comprising:

(a) attaching a first component to the reactive group on the optical fiber of the first region and a first component to the reactive group on the optical fiber of the second region; and (b) delivering a first activator to the first component on the optical fiber of the first region via the optical fiber of the first region and a second activator to the first component on the optical fiber of the second region via the optical fiber of the second region.

Functionalization of the Optical Fiber

The optical fibers can be made of any material which is capable of transmitting an activator. In preferred embodiments, the activator is heat and/or light. In preferred embodiments, the fibers will be constructed from glass, quartz or plastic. Accordingly, any and all compositions presently known or to be employed in the future as an optic fiber strand may be used to make the present invention without limitation. Examples of fibers useful in practicing the instant invention include a 350 μm-diameter imaging fiber available from Sumitomo Electric Industries (Torrance, Calif. U.S.A.) and a 500 μm-diameter fiber available from SpecTran Communication Fiber Technologies, Inc. (Sturbridge, Mass. U.S.A.). In a preferred embodiment, the fibers are made of glass.

According to the present invention, a fiber's surface is functionalized by covalently binding a functionalizing reagent to the fiber surface in such a way as to derivatize the fiber surface with a plurality of available reactive functional groups. Functional groups which can be used in practicing the present invention include, for example, amines, hydroxyl groups, carboxylates, olefins, sulfhydryls, etc. A wide variety of reaction types is available for the functionalization of the fiber surface. For example fibers constructed of a plastic such as polypropylene, can be surface derivatized by chromic acid oxidation, and subsequently converted to hydroxylated or aminomethylated surfaces. Fibers made from highly crosslinked divinylbenzene can be surface derivatized by chloromethylation and subsequent functional group manipulation. When the fibers are constructed of a siliceous material such as glass, the surface can be derivatized by reacting the surface Si—OH, SiO—H, and/or Si—Si groups with a functionalizing reagent.

In a preferred embodiment, wherein the fibers are made from glass, the covalent bonding of the reactive group to the glass surface is achieved by conversion of groups on the fiber's surface by a silicon modifying reagent such as:

$$(RO)_3—Si—R^1—X \tag{1}$$

where R is an alkyl group, such as methyl, $R^1$ is a linking group between silicon and X and X is a reactive group or a protected reactive group.

The $R^1$ groups are either stable or they can be cleaved by chemical or photochemical reactions. For example, $R^1$ groups comprising ester or disulfide bonds can be cleaved by hydrolysis and reduction, respectively. Also within the scope of the present invention is the use of $R^1$ groups which are cleaved by light such as, for example, nitrobenzyl derivatives, phenacyl groups, benzoin esters, etc.

The reactive functional groups (X) are, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups which can be converted to disulfides or reacted with acyl halides;

(h) amine or sulfhydryl groups which can be, for example, acylated or alkylated;

(i) alkenes which can undergo, for example, cycloadditions, acylation, Michael addition, etc.; and (j) epoxides which can react with, for example, amines and hydroxyl compounds.

The reactive groups can be chosen such that they do not participate in, or interfere with, the reaction attaching the functionalizing group onto the fiber's surface. Alternatively, the reactive group can be protected from participating in the reaction by the presence of a protecting group. Those of skill in the art will understand how to protect a particular functional group from interfering with a chosen set of reaction conditions. For examples of useful protecting groups, see, Greene, T., et al., PROTECTIVE GROUPS IN ORGANIC SYNTHESIS, John Wiley & Sons, New York, 1991.

In a preferred embodiment, the reactive groups are selected from the group consisting of amines, sulfhydryls, olefins and epoxides. In another preferred embodiment, the reactive groups are tethered to the optical fiber by means of a commercially available reagent (Aldrich Chemical Company, Milwaukee, Wis., U.S.A.) such as, for example, N-[3-(trimethoxysilyl)propyl]-ethylenediamine, (3-mercaptopropyl)trimethoxysilane, (3-chloropropyl) trimethoxysilane, 3-aminopropyltrimethoxysilane, N-[3-(trimethoxysilyl)propyl]-N'-(4vinylbenzyl)ethylenediamine, N'-[3-(trimethoxysilyl)propyl] diethylenetriamine and 3glycidoxypropyltrimethoxysilane.

In another preferred embodiment, the functionalizing reagent provides for more than one reactive group per each reagent molecule. Using reagents such as compound 2, below, each reactive site on the fiber surface is, in essence, "amplified" by conversion to two or more functional groups.

$$(RO)_3—Si—R^1—(X)_n \qquad (2)$$

where R, $R^1$ and X are substantially as described above for compound 1.

In a preferred embodiment, the first building block component of the nascent product is attached directly and essentially irreversibly via a "stable bond" to the functional group on the surface of the fiber. A "stable bond", as used herein, is a bond which maintains its chemical integrity over a wide range of conditions (e.g., amide, carbamate, carbon—carbon, ether, etc.). In another preferred embodiment, the first building block component can be attached to the fiber surface by a "cleavable bond". A "cleavable bond", as used herein, is a bond which is designed to undergo scission under conditions which do not degrade other bonds in the product molecule. Cleavable bonds include, but are not limited to, disulfide, imine and ester bonds. A framework representation of the constructs of these embodiments is displayed below:

(3)

where X is the reactive group tethered to the optical fiber and Y is the first building block component. The bond formed between X and Y can be either stable or cleavable.

In another embodiment, the first building block is attached via a "spacer arm" which is interposed between the fiber surface and the first building block. As used herein, "spacer arm" refers to bifunctional groups which can crosslink the reactive groups on the fiber surface with the first building block component. Spacer arms are used for several purposes including, for example, increasing the hydrophobicity or hydrophilicity of the fiber surface, increasing the distance between the fiber surface and the first building block and adding surface activity (surfactant properties) to the fiber surface. The first building block is attached to the spacer by a bond which is either stable or cleavable, as described above. A representation of the embodiments utilizing a spacer arm is displayed below:

(4)

where X and Y are as described above and Z is a spacer arm. In this construct, the bonds between X, Z and Y are independently chosen from stable and cleavable bonds. Thus, in one preferred embodiment, the product molecule is cleavable from the support-spacer construct. In another preferred embodiment, the product molecule-spacer construct is cleavable from the optical fiber.

The hydrophobicity of the fiber surface can be increased by using a hydrophobic spacer arm such as, for example, long chain diamines, α, ω-amino acids, etc. Representative hydrophobic linking compounds include, but are not limited to, 1,6-hexanediamine, 1,8-octanediamine, 6-aminohexanoic acid and 8-aminooctanoic acid.

The hydrophilicity of the fiber surface can be enhanced by reaction with polar molecules such as amine, hydroxyl and polyhydroxyl containing molecules. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991, which is incorporated herein by reference.

The fiber surface can also be made surface-active by attaching to the fiber surface a spacer which has surfactant properties. Compounds useful for this purpose include, for example, aminated or hydroxylated detergent molecules such as, for example, 1-aminododecanoic acid.

In another embodiment, the spacer serves to distance the first building block from the fiber surface and/or other first building blocks. Spacers with this characteristic have several uses. For example, a molecule held too closely to the fiber surface may not react with incoming building blocks, or it may react unacceptably slowly. When a component (building block) of the desired product molecule, or the product molecule itself, is sterically demanding the reaction leading to product formation can be undesirably slowed, or not occur at all, due to the monolithic fiber hindering the approach of the two components. The spacer arm can also facilitate the screening of the compounds bound to the fiber. In certain instances, the product molecule is nestled so closely to the fiber surface that the species which is being used to screen for the product's activity cannot effectively bind the molecules on the fiber surface. This difficulty can be overcome by use of a spacer arm which allows the maintenance of an adequate distance between the product molecule and the fiber surface.

In each of the above-described embodiments, the spacer arm can be a component of the first building block such that the spacer and building block are attached to the fiber as a cassette. Alternatively, the fiber can be derivatized with the spacer and the spacer subsequently derivatized with the first building block.

In another embodiment, the physical characteristics (e.g., hydrophobicity, hydrophilicity, surface activity) of the fiber surface are altered by attaching a monovalent moiety which is not intended to bear the first building block. As used herein, "monovalent moiety" refers to organic molecules with only one reactive functional group. "Monovalent moieties" are to be contrasted with the bifunctional "spacer" groups described above. Such monovalent groups are used to modify the hydrophilicity, hydrophobicity, binding characteristics, etc. of the fiber surface. Examples of groups useful for this purpose include long chain alcohols, amines, fatty acids, fatty acid derivatives, poly(ethyleneglycol) monomethyl ethers, etc. In one embodiment, the monovalent moiety groups are attached to the fiber's surface prior to attaching the first building block or spacer arm by "underlabeling" the surface functional groups with less than a stoichiometric equivalent of the monovalent moiety. This strategy modifies the fiber surface while leaving reactive groups available for immobilizing the first building block component.

Other, reactive groups, spacer arms, monovalent moieties and protocols for attaching these groups to the optical fiber's surface will be apparent to those of skill in the art.

Reaction Types

The following discussion provides an overview of types of reactions in which the present invention finds use. This discussion is not intended to be exhaustive and neither limits nor defines the scope of the invention. Additional reactions which can be practiced using the method of the invention will be apparent to those of skill in the art. In general, the methods of the instant invention will find use in conjunction with those broad classes of reactions which are facilitated by exposing the reactants to light, heat or a combination thereof. For a review of the synthetic applications of photochemical reactions, see, Schoenberg, A., PREPARATIVE ORGANIC PHOTOCHEMISTRY, New York, Springer-Verlag, 1968, the disclosure of which is incorporated herein by reference. Reactions which are facilitated by the application of heat are well known in the art. For a general survey, see, March, J. ADVANCED ORGANIC CHEMISTRY, John Wiley & Sons, New York 1985, the disclosure of which is incorporated herein by reference.

Once the first building block is tethered to the optical fiber, either directly or through a spacer arm, it is possible to carry out a wide variety of reactions using the first building block as a substrate. In one embodiment, the first building block component undergoes a light- or heat-induced intramolecular reaction to afford a new molecule. In another embodiment, the first building block is contacted with a second building block and a light or heat induced coupling between the first building block and the second building block occurs. The process of contacting the tethered building blocks with additional building blocks and irradiating with either light or heat continues until the desired array of compounds is produced. Because of the wide variety of reaction types which are amenable to induction or facilitation by light, heat or a combination thereof, the present invention provides access to a vast number of individual compounds and arrays containing those compounds.

Reactions which are facilitated or induced by the application of light and which can be practiced using the method of the present invention include, but are not limited to photocleavage, decomposition of starting molecules into new molecules, photoisomerization, hydrogen-atom abstraction, photodimerization, photopolymerization, annulation, oxidation and reduction. These and other photochemical reactions are known to those of skill in the art. The above list and the discussion which follows are intended to be generally illustrative of reaction types which can be performed using the instant invention. Thus, neither the list nor the discussion define or limit the scope of photochemical reactions with which the instant invention can be practiced.

The scope of the instant invention encompasses performing each of the above-referenced reaction types by either direct irradiation of a substrate, or alternatively, by the use of photosensitizing agents (e.g., benzene, benzyl, pyrene, perylene, etc.). Additionally, the photochemical transformations can be effected by irradiation alone or by the combination of irradiation and a catalyst. Examples of useful catalysts include copper triflate (ORGANIC SYNTHESIS COLLECTIVE VOLUME 7, John Wiley & Sons, New York 1990, pp. 177–181), $Ti(CH_2Ph)_4$ (Cannell, *J. Am. Chem. Soc.*, 94:6867 (1972)) and zeolites (Schipperijn, et al., *Tetrahedron Lett.*, 231 (1972)). Other catalysts and photosensitizers which are within the scope of the instant invention will be apparent to those of skill in the art.

The present invention can also be used to produce new compounds via the photoinduced cleavage of molecules tethered to the optical fiber. A number of reactions are initiated by the cleavage of a sigma bond and result in net rearrangement, fragmentation or elimination of a small molecule (e.g., $N_2$, $CO$, $CO_2$, etc.). Photocleavage reactions are generally classified as either homolytic cleavage or heterolytic cleavage. In a homolytic cleavage, a sigma bond is cleaved to produce a radical pair or a diradical. In a heterolytic cleavage, a sigma bond is cleaved to produce an ion pair or a zwitterion. Appropriate substrates for photocleavage include, for example, ketones, lactones, esters, amides, cyclobutanones, cyclopropanes, epoxyketones, β, γ-unsaturated ketones, azides, diazo compounds and azirines. Carbonyl compounds such as, for example, dialkyl and alkylaryl ketones are α-cleaved to produce radical pairs. The radical pairs produced by α-cleavage can undergo further reactions such as radical recombinations, disproportionation or decarbonylation. See, ORGANIC SYNTHESIS COLLECTIVE VOLUME 5, John Wiley & Sons, New York, 1973, pp. 297–298. Both linear and cyclic compounds can be photocleaved using the instant invention. In general, the products resulting from α-cleavage of cyclic compounds are analogous to those derived from α-cleavage of linear compounds. See, Dalton, J. C., et al., *J. Am. Chem. Soc.*, 93:7213 (1971).

Thus, in one embodiment, a lactone is tethered to the optical fiber and photolyzed to eliminate $CO_2$. In another embodiment, a cyclic ketone tethered to the optical fiber is photolyzed to produce a ring contracted analogue of the starting ketone. Redmore, et al., *Adv. Alicyclic Chem.*, 3:1–138 (1971). Reactions involving nitrogen extrusion can also be practiced using the present invention. Thus, a 1-pyrazoline tethered to the optical fiber is photolyzed to produce the corresponding cyclopropane. In a further embodiment, a triazoline is irradiated to afford the corresponding aziridine. Similarly, an immobilized pyrazole can be converted to the corresponding cyclopropane via photolysis. Adam, et al., *Angew. Chemie. Int. Ed. Engl.*, 19:762–779 (1980).

When the photochemical reaction involves cleaving the substrate such that free radicals are produced, the species undergoing cleavage can be, for example, aldehydes, ketones, anhydrides, esters (i.e., Norrish Type I and Norrish Type II cleavage), peroxy compounds and aliphatic azo compounds. When the molecules undergoing cleavage produce, as a result of that cleavage, two different radical species, the molecule are tethered to the fiber optic support in such a way that one of the two species remains tethered to the support and the other is free to enter the surrounding solution.

In one embodiment, the cleavage follows the motif of the Reed reaction and results in the chlorosulfonylation of a molecule immobilized on the optical fiber. Gilbert, SULFONYLATION AND RELATED REACTIONS, Interscience, New York, 1965, pp. 126–131. In another embodiment, the cleavage leads to the coupling of two aryl groups. For example, an immobilized aryl iodide is photolyzed in the presence of a second aryl moiety. Photolysis of the carbon-iodine bond followed by coupling of the resulting intermediate with a second aryl moiety affords a diaryl compound. Similar reactions are available using immobilized ArTl $(OCOCF_3)_2$ compounds. Sharma, et al., *Angew. Chemie Int. Ed. Engl.*, 7:36–44 (1968).

Molecules having multiple bonds can undergo isomerization, such as cis-trans isomerization, upon irradiation with ultraviolet light. For example, compounds such as cis-stilbene and its derivatives are readily converted to the corresponding trans-isomers. This type of isomerization can also occur with compounds which have anti- and syn-isomers, such as organic azo compounds. Another type of isomerization of use with the instant invention is the sigmatropic rearrangement. In these rearrangements, a sigma bond moves from one position to another along a conjugated framework. See, Spangler, *Chem. Rev.*, 76:187–217 (1976). Also within the scope of the instant invention is the use of the di-π-methane rearrangement pathway. Hixson, et al., *Chem. Rev.*, 73:531 (1973). Using the di-π-methane rearrangement pathway a 1,4-diene with C-3 alkyl or aryl substituent which is tethered to the optical fiber can be converted to a vinyl cyclopropane. Similarly, a tethered allylbenzene can be converted to a benzyl cyclopropane.

Other types of isomerizations include the isomerization of double bonds into rings (i.e., annulation) such as, for example, the conversion of 2,5-norbornadiene to quadricyclane (ORGANIC SYNTHESIS COLLECTIVE VOLUME 6, John Wiley & Sons, New York 1988, pp. 962–964) and the conversion of carvone to carvonecamphor and other similar photocycloadditions (Buchi, et al., *J. Am. Chem. Soc.*, 79:4741 (1957)). In general, the annulations will comprise [2+2] photocycloadditions, however, any allowed photochemical cyclization (i.e., 4n total electrons involved in the reaction) is within the scope of the instant invention.

Hydrogen-atom abstractions from certain molecules can be induced photochemically. An example of a hydrogen atom abstraction is the synthesis of benzhydrol or benzpinacol from benzophenone. March, J. ADVANCED ORGANIC CHEMISTRY, John Wiley & Sons, New York 1985, p.216.

Photodimerization and photopolymerization are further examples of photoinduced reactions which can be practiced using the present invention. When these processes are utilized, substrate molecules can be used such as, for example, conjugated dienes, α, β-unsaturated ketones (e.g., cyclopentenone), acids or acid derivatives or quinones. Eaton, J., *Am. Chem. Soc.*, 84:2344, 2454 (1962). In embodiments of the invention wherein the desired product is a dimer or a polymer of a photoactive species, the photoreactive monomer is first tethered to the optical fiber. The optical fiber is then immersed into the liquid monomer or a solution containing the monomer and the irradiation is performed. The irradiation step is repeated as often as is necessary or feasible to produce dimers and higher polymers.

Intermolecular cyclizations can also be carried out using the methods and apparatus of the present invention. Similar to the intramolecular cyclizations discussed above, the intermolecular cyclizations will generally be [2+2] cyclizations, however, the invention is practicable with any photochemically accessible type of cyclization. Examples of cyclized compounds which can be synthesized using the instant invention include functionalized and unfunctionalized cyclopropanes, cyclobutanes, cyclopentanes, cyclohexanes and higher hydrocarbon ring systems, heterocyclic rings and fused ring systems. Fused ring systems can comprise hydrocarbon rings, heterocyclic rings and combinations thereof.

Specific examples of intermolecular cyclizations include the formation of bicyclic compounds by irradiating mixtures of cyclohexenones and ethylenes. Owsley, et al., *J. Chem. Soc.*, p. 3445 (1971). Irradiating mixtures of benzoquinones with acetylenes provides access to unsaturated bicyclic systems. Pappas, et al., *Tetrahedron Lett.* p. 1597 (1967). Ring systems can be formed by combining organohalides and ethylenes. ORGANIC SYNTHESIS COLLECTIVE VOLUME 6, John Wiley & Sons, New York, 1988, pp. 974–975. The components which come together to form the ring system can also be two molecules of the same substrate. For example, butadiene can be photochemically dimerized to afford 1,2-divinylcyclobutane.

In those embodiments of the invention involving intermolecular cyclizations, one component of the nascent ring is tethered to the optical fiber. The other component is present as a pure liquid, a solution, a suspension, or in the gas phase. In general, the component to be tethered is chosen for the presence of functional groups which allow this component to be attached to the optical fiber.

Photochemical reactions of ring systems include ring expansion, ring contraction and the conversion of rings to linear moieties. These general types of reactions are within the scope of the present invention. An exemplary reaction type, the ring expansion reaction, can be photochemically induced in both hydrocarbon and heterocyclic ring systems. Hydrocarbon ring expansion encompasses reactions such as, for example, the 1,3-cyclohexadiene to 1,3,5 triene conversion such as, for example, the conversion of norcaradiene to cycloheptatriene. Maier, *Angew. Chem. Int. Ed. Engl.*, 6:402–413 (1967). Ring contractions include, for example, the conversion of 2-ethoxypyrroline-5-ones to cyclopropanes. See, ORGANIC SYNTHESIS COLLECTIVE VOLUME 6, John Wiley & Sons, New York, 1988, pp. 226–232. Other photochemically mediated ring expansion and contraction reactions which can be practiced using the methods and apparatus of the present invention will be apparent to those of skill in the art.

Photooxidation reactions are also within the scope of the present invention. Photooxidation reactions are typically encountered as photochemical halogen additions across carbon-hydrogen sigma bonds. These oxidations are facilely performed on a wide variety of substrates using either bromine or chlorine donor molecules. Sosnovsky, G., FREE RADICAL REACTIONS IN PREPARATIVE ORGANIC CHEMISTRY, Macmillan, New York, 1964, pp. 282–331.

Of the various classes of photoaddition reactions, photoreduction is very commonly encountered in the art. For a review of the synthetic applications of photoreductions, see: Schoenberg, A., PREPARATIVE ORGANIC PHOTOCHEMISTRY, New York: Springer-Verlag, 1968. A prototype photoreduction reaction is the reductive addition of hydrogen, from a hydrogen-donor molecule, to a double bond such as, for example an alkene or carbonyl functionality. The products isolated from such reactions are alkanes and alcohols, respectively. Another class of photoreductions occur by an intramolecular process; the hydrogen-donor and hydrogen-acceptor are both components of the same molecule. Lewis, F. D., et al., *Molec. Photochem.*, 2:259 (1970).

Reactions which are facilitated by the addition of energy in the form of heat are known to those of skill in the art. See, March, J., ADVANCED ORGANIC CHEMISTRY, John Wiley & Sons, New York, 1985, pp. 180–181. Reactions which are facilitated by heat include, but are not limited to, aliphatic and aromatic nucleophilic substitution, aromatic electrophilic substitution, additions to carbon—carbon multiple bonds, addition to carbon-hetero multiple bonds, cycloadditions, eliminations, oxidations and reductions.

Combinatorial Library Components

The individual components of the combinatorial library will generally be compounds which are bioactive. The combinatorial library itself will generally be characterized by a spectrum of bioactivity as the structures of the individual compounds are varied over the library. A compound's bioactivity can be primarily pharmacological, herbicidal, pesticidal, etc. The compounds of the library can be involved in, for example, cell-pathogen, cell—cell, pathogen-extracellular matrix and pathogen—pathogen interactions. In preferred embodiments, the compounds can comprise drugs or compounds which exhibit pharmacological activity. It will be understood by those of skill in the art that a single compound can have more than one biological effect and/or can be useful in the treatment of more than one disease state.

In a preferred embodiment, the array comprises at least 10 different compounds. In more preferred embodiment, at least 50 different compounds are made. In a further preferred embodiment, at least 100 different compounds are made. In an even more preferred embodiment, at least 1000, and more preferably at least 10,000, different compounds are made.

In one embodiment, libraries of compounds are prepared using the instant invention by varying the identity of substituents (i.e., R groups) on a nucleus common to all of the individual components of the library. In another embodiment, the nucleus is varied across the compounds of the library. In yet another embodiment, both the substituents and the nuclei are varied over the library.

The R groups pendant from the nucleus are chosen for the characteristics which they impart to the overall molecular construct. R groups affect the reactivity and stability of compounds. The size and electronic nature of the R groups is varied to alter the bulk around the nucleus and the electronic properties of the compound. R groups which are chiral impart chirality to the compound. Further, R groups are used to adjust the hydrophobicity/hydrophilicity of the compound.

The R groups are independently selected from the group consisting of alkyl, substituted alkyl, aryl, substituted aryl, arylalkyl, substituted arylalkyl, acyl, halogen, amino, cyano, nitro, hydroxy, alkoxy, alkylamino, acylamino, aryloxy, aryloxyalkyl, substituted aryloxyalkyl, heteroaryl, substituted heteroaryl, heteroarylalkyl, substituted heteroarylalkyl, heterocycles, substituted heterocycles, heterocyclicalkyl, substituted heterocyclicalkyl S-aryl and S-alkyl mercaptans.

The term "independently selected" is used herein to indicate that the R groups, e.g., $R_1$, $R_2$ and $R_3$, can be identical or different (e.g., $R_1$, $R_2$ and $R_3$ may all be substituted alkyls or $R_1$, and $R_2$ may be a substituted alkyl and $R_3$ may be an aryl, etc.).

A named R group will generally have the structure which is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated, monovalent hydrocarbon radical having from 1–12 carbons and preferably, from 1–6 carbons. When the alkyl group has from 1–6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc. As used herein, the term encompasses "substituted alkyls."

"Substituted alkyl" refers to alkyl as just described including one or more functional groups such as lower alkyl, aryl, acyl, halogen (i.e., alkylhalos, e.g., $CF_3$), hydroxy, amino, alkoxy, alkylamino, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl."

The term "arylalkyl" is used herein to refer to a subset of "aryl" in which the aryl group is attached through an alkyl group as defined herein.

"Substituted aryl" refers to aryl as just described including one or more functional groups such as lower alkyl, acyl, halogen, alkylhalos (e.g., $CF_3$), hydroxy, amino, alkoxy, alkylamino, acylamino, acyloxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

"Substituted arylalkyl" defines a subset of "substituted aryl" wherein the substituted aryl group is attached to the nucleus by an alkyl group as defined herein.

The term "acyl" is used to describe a ketone substituent, —C(O)R, where R is alkyl or substituted alkyl, aryl or substituted aryl as defined herein.

The term "halogen" is used herein to refer to fluorine, bromine, chlorine and iodine atoms.

The term "hydroxy" is used herein to refer to the group —OH.

The term "amino" is used herein to refer to the group —NRR', where R and R' may independently be hydrogen, lower alkyl, substituted lower alkyl, aryl, substituted aryl or acyl.

The term "cyano" is used herein to refer to the group —CN.

The term "nitro" is used herein to refer to the —$NO_2$ group.

The term "alkoxy" is used herein to refer to the —OR group, where R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkylamino" denotes secondary and tertiary amines wherein the alkyl groups may be either the same or different and may consist of straight or branched, saturated or unsaturated hydrocarbons.

As used herein, the term "acylamino" describes substituents of the general formula RC(O)NR', wherein R' is a lower alkyl group and R represents the nucleus shown in Formula 1 or an alkyl group, as defined herein, attached to the nucleus.

The term "acyloxy" is used herein to describe an organic radical derived from an organic acid by the removal of the acidic hydrogen. Simple acyloxy groups include, for example, acetoxy, and higher homologues derived from carboxylic acids such as ethanoic, propanoic, butanoic, etc. The acyloxy moiety may be oriented as either a forward or reverse ester (i.e., RC(O)OR' or R'OC(O)R, respectively, wherein R comprises the portion of the ester attached either directly or through an intermediate hydrocarbon chain to the nucleus).

As used herein, the term "aryloxy" denotes aromatic groups which are linked to the nucleus directly through an oxygen atom. This term encompasses "substituted aryloxy" moieties in which the aromatic group is substituted as described above for "substituted aryl."

Figure 1:
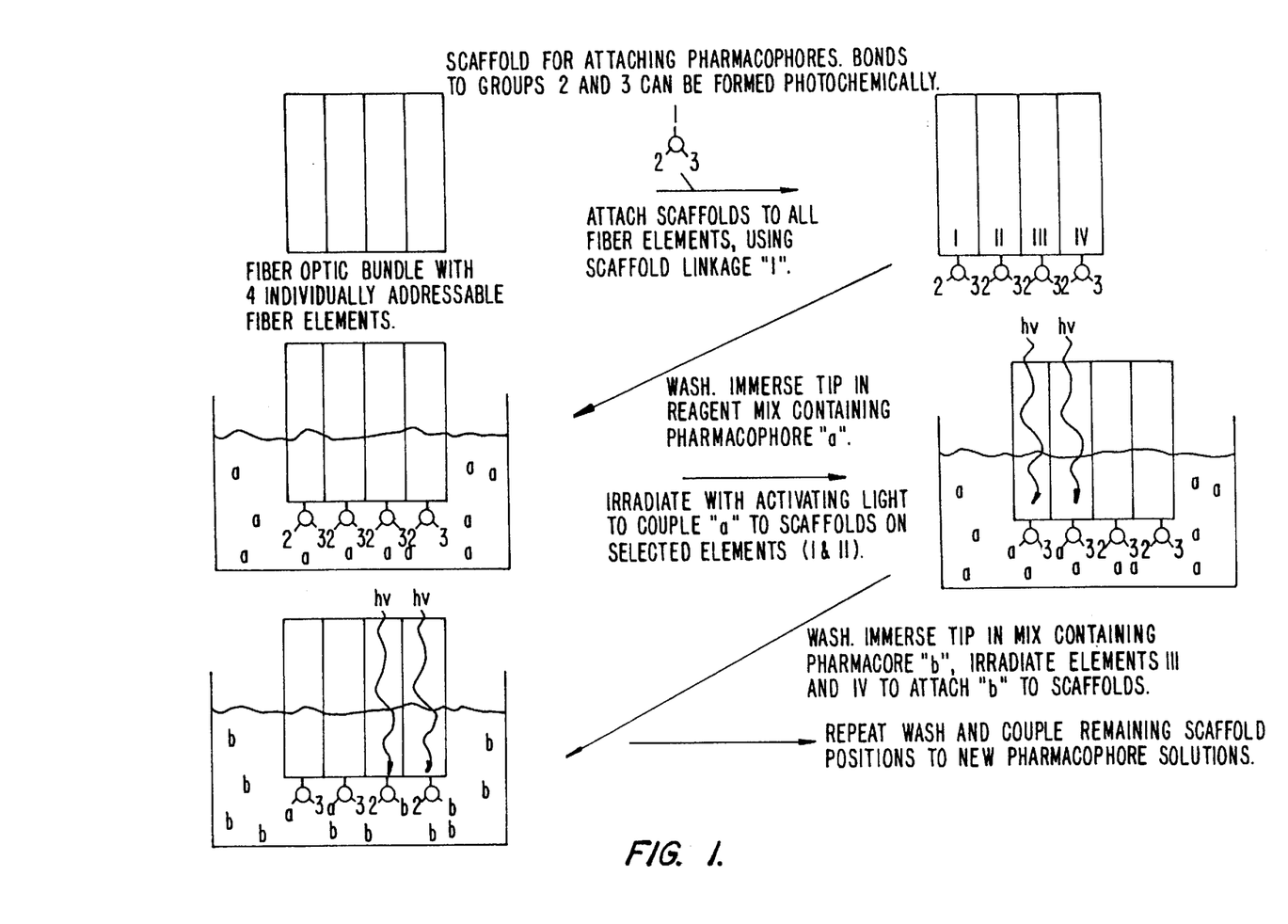
FIG. 1 is a schematic of the method of the invention wherein the optical fibers of region 1 and region 2 are oriented contiguously.
Figure 2:
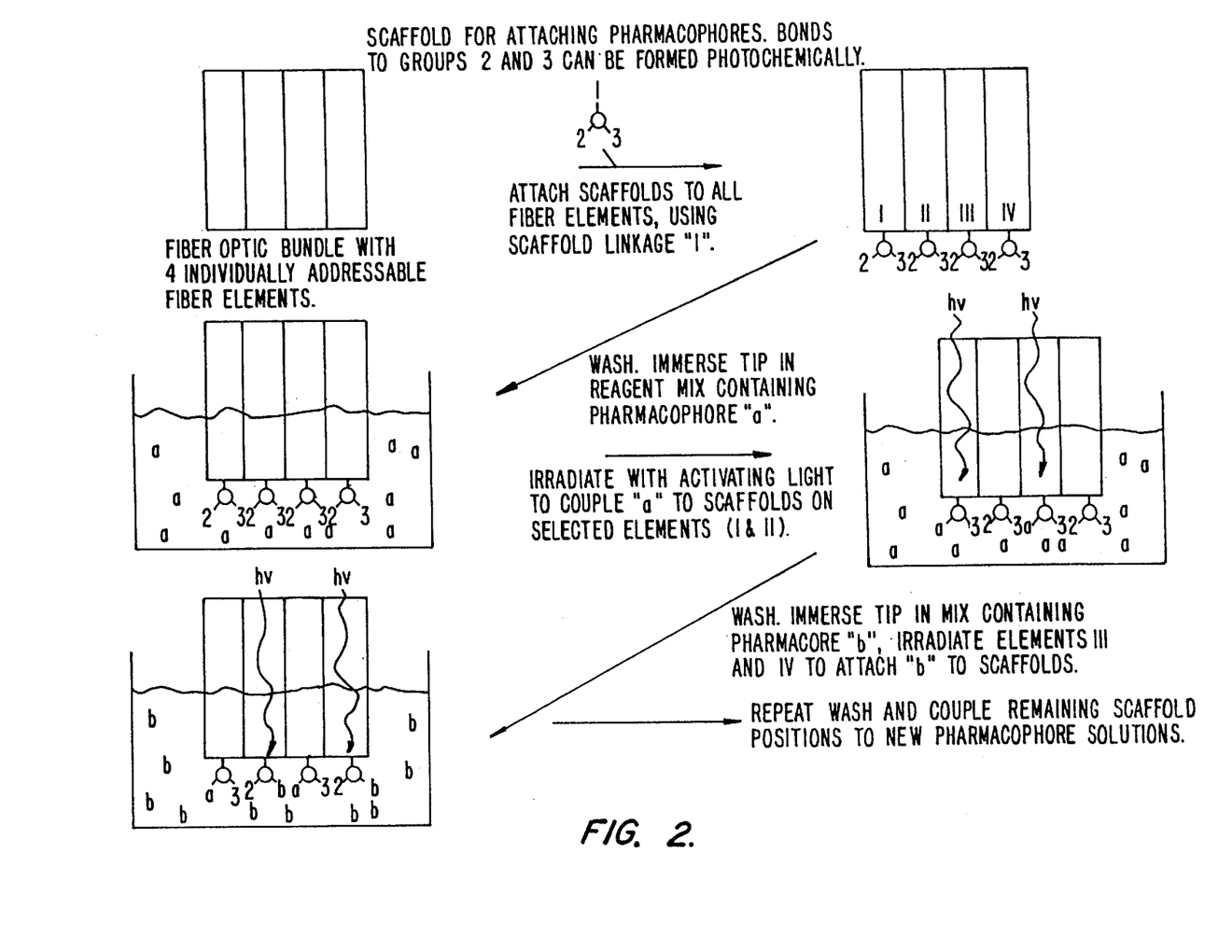
FIG. 2 is a schematic diagram of the invention wherein the optical fibers of region 1 and region 2 are oriented non-contiguously.
Figure 3:
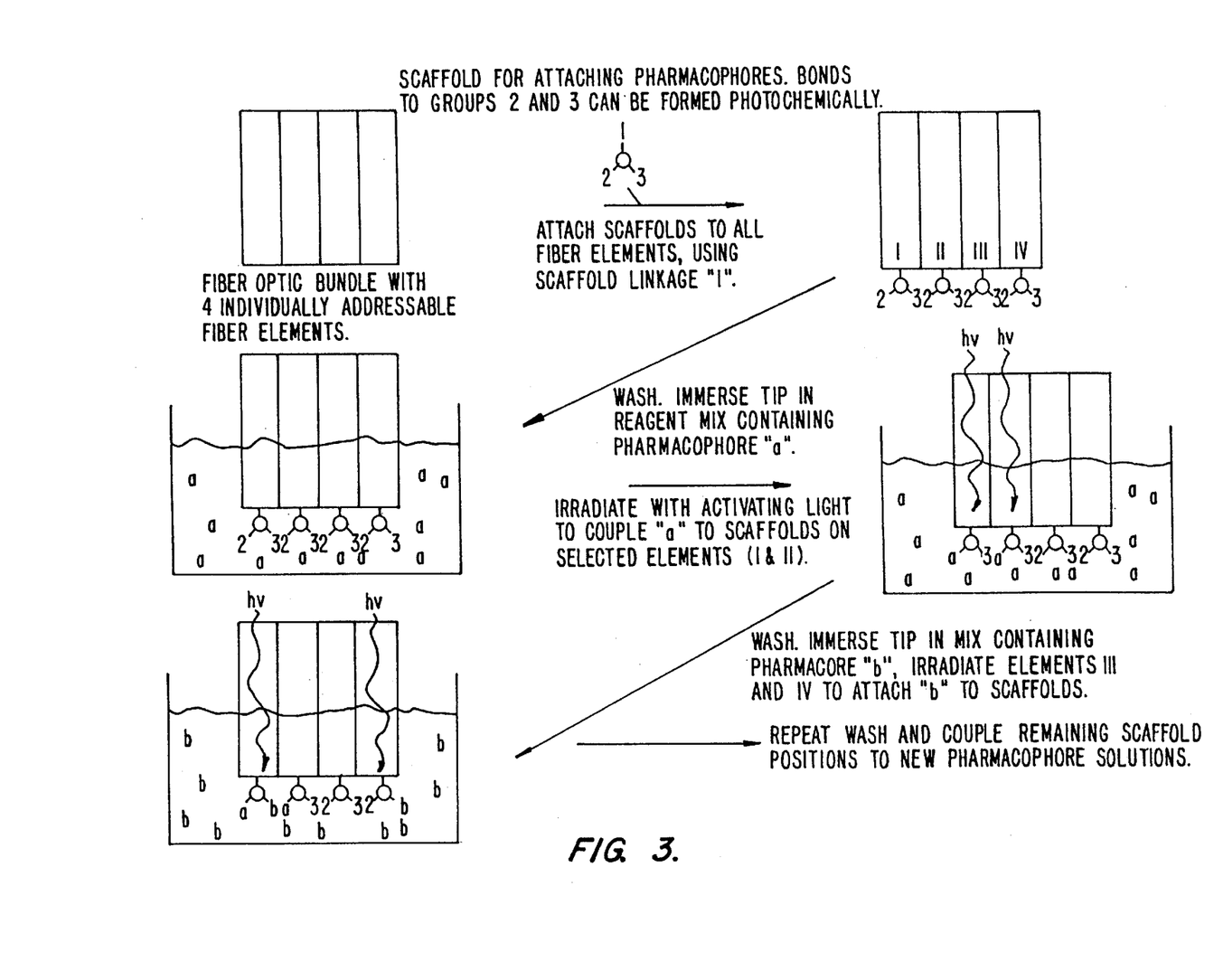
FIG. 3 is a schematic diagram of the method of the invention wherein the optical fibers of region 1 are oriented contiguously and the optical fibers of region 2 are oriented non-contiguously.

As used herein "aryloxyalkyl" defines aromatic groups attached, through an oxygen atom to an alkyl group, as defined herein. The alkyl group is attached to the nucleus shown in FIG. 1. The term "aryloxyalkyl" encompasses "substituted aryloxyalkyl" moieties in which the aromatic group is substituted as described for "substituted aryl."

As used herein, the term "mercapto" defines moieties of the general structure R—S—R' wherein R and R' are the same or different and are alkyl, aryl or heterocyclic as described herein.

The term "saturated cyclic hydrocarbon" denotes groups such as the cyclopropyl, cyclobutyl, cyclopentyl, etc., and substituted analogues of these structures.

The term "unsaturated cyclic hydrocarbon" is used to describe a monovalent non-aromatic group with at least one double bond, such as cyclopentene, cyclohexene, etc. and substituted analogues thereof.

The term "heteroaryl" as used herein refers to aromatic rings in which one or more carbon atoms of the aromatic ring(s) are substituted by a heteroatom such as nitrogen, oxygen or sulfur. Heteroaryl refers to structures which may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "heteroaryl" wherein the heteroaryl group is attached through an alkyl group as defined herein.

"Substituted heteroaryl" refers to heteroaryl as just described wherein the heteroaryl nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted heteroaryl" as described above in which an alkyl group, as defined herein, links the heteroaryl group to the nucleus.

The term "heterocyclic" is used herein to describe a monovalent saturated or unsaturated non-aromatic group having a single ring or multiple condensed rings from 1–12 carbon atoms and from 1–4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc.

The term "heterocyclicalkyl" defines a subset of "heterocyclic" wherein an alkyl group, as defined herein, links the heterocyclic group to the nucleus.

The term "substituted heterocyclicalkyl" defines a subset of "heterocyclic alkyl" wherein the heterocyclic nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc.

By manipulating the R groups and/or the nucleus of the compounds of the library, the synthesis and screening of libraries of drugs which have an effect on the central nervous system are provided for. For example libraries of drugs which are useful for, but not limited to, the treatment of Alzheimer's disease, acute and/or chronic pain, alcohol dependence, narcotic dependence can be assembled and screened. Further, libraries of hypnotics, antitussives, antianxiolytics, antimigraines and anti-motion sickness agents can be prepared. Other libraries which are accessible using the method of the present invention include arrays of muscle relaxants, antinausea drugs, parasympatholytics, parasympathomimetics, psychotropics, antidepressants, antipsychotics, psychostimulants, sedatives, antiseizure medications, sympatholytics, anticonvulsants and drugs used to treat diseases such as, for example, multiple sclerosis.

Libraries of compounds with activities directed towards the cardiovascular system can be assembled and screened.

These libraries include, for example, adrenergic agents, angiotensin converting enzyme inhibitors, angiotensin II receptor antagonists, antiarythmics, β-blockers, calcium channel blockers, etc. Arrays of diuretics, vasodilators, vasopressors, hypolipidemics and antihypertensives are also available by the method of the invention. Other libraries include anticoagulants, antithrombins and platelet inhibitors.

Anti-cancer chemotherapeutic libraries can also be assembled and screened using the method of the invention. Thus, libraries of, for example, anti-androgens, cytocidal agents, anti-estrogens, antimetabolites and hormones are accessible.

In other embodiments, the library is an array of compounds suitable for gastrointestinal applications. Thus, arrays of drugs are available which act as antispasmodics, anticholinergics, appetite suppressants, antidiarrheal and proton pump inhibitors. Additional libraries include drugs with an endocrine modulatory activity such as, for example, contraceptives, diabetes modulators, anabolic steroids, androgens, antidiuretics, thyroid agents, anti-thyroid agents, hyperprolactinemic modulators and prostaglandins. Arrays of drugs with dermatological effects can also be prepared and screened for activity. Thus, agents such as, for example, anti-acne agents and antipruritics can be synthesized and examined for activity.

Compounds which regulate the respiratory system can also be prepared in a library format. Drugs such as, for example, mucolytics, antiinflammatory agents, bronchodilators and antihistamines can be components of a library.

Immunomodulatory agents can also be prepared as an array and screened for activity. Thus, using the method of the invention libraries can be prepared which comprise steroids, histamine $H_2$ antagonists, immunosuppressants and antiinflammatory agents.

Other libraries can comprise antimicrobial agents such as, for example, quinolines, sulfonamides, antivirals, reverse transcriptase inhibitors, protease inhibitors, antiparasitic agents or antifungals.

Urinary tract agents can also be library components. Such compounds include, but are not limited to, uricosuric agents, antimicrobials, antispasmodics, prostatic hypertrophy modifiers and compounds used in the treatment of cystitis.

Screening the Array

Once formed, the array of compounds can be screened/assayed for useful properties. Properties which can be screened for include, but are not limited to, the following properties: biological activities, binding affinities, biological properties, pharmacological properties, oral bioavailabilities, circulatory half-lives, agonist activities, antagonist activities, solubilities, etc. The array of compounds can be screened for useful properties sequentially or in parallel. Additionally, the array can be screened in situ or, alternatively, the library can be screened other than in situ. Once identified, the library compounds having useful properties can be prepared on a large-scale. Methods of screening libraries are described in, COMBINATORIAL LIBRARIES: SYNTHESIS, SCREENING, AND APPLICATION POTENTIAL, Cortese, R., Ed., Walter de Gruyter, Berlin, 1996, pp. 159–174, which is incorporated herein by reference.

The use of optical fibers as library supports presents a unique opportunity for assaying the library in situ. Methods such as, for example, ultraviolet, visible, infrared, raman and fluorescence spectroscopy can all be used to analyze the structure of the compounds bound to the optical fiber and the compound's characteristics when it is in the presence of a putative receptor for the compound.

Thus, in one embodiment, the binding of a target molecule which is spectroscopically active to a library compound is assayed by spectroscopy while the library compound is attached to the fiber optic. In a preferred embodiments, the target molecule which binds to the library compounds is labeled with a unique spectroscopic probe (e.g., chromophore, fluorophore, etc.). In a particularly preferred embodiment, the spectroscopic probe is a fluorophore.

In its simplest form, the spectroscopic experiment consists of incubating the library, while attached to the optical fiber, with a solution of the labeled target molecule. Following this incubation, the library is removed from the solution and washed to remove target molecule which is adventitiously and non-specifically bound to the library array. The library is then spectroscopically examined by using the optical fibers to both supply light to the labeled-target molecule and to receive the modified light back from the target molecule. By way of example, an instrument appropriate for analysis of a library using fluorescent spectroscopy is described below.

A simple generalized instrument suitable for fluorescence spectrophotometry usually comprises: a source of light energy, a primary filter or excitation monochromator, a secondary filter or emission monochromator, a photodetector and a readout device. The primary filter or monochromator selects specific bands or wavelengths of radiation from the light source and directs them through the sample. The secondary emission or fluorescence is isolated by the secondary filter or monochromator and directed to the photodetector which measures the intensity of the emitted radiation.

For more complete and detailed information, the following publications and references are provided, the disclosure of which is expressly incorporated by reference herein: Willard, Merritt, Dean and Settle, INSTRUMENTAL METHODS OF ANALYSIS, 6th ed., Wadsworth Publishing Company, Belmont, Calif., 1981; Kakowicz, J. R., PRINCIPLES OF FLUORESCENCE SPECTROSCOPY, Plenum Press, New York, 1983.

In one embodiment, the instrument used for fluorescence detection and imaging is a modified epifluorescence microscope (Olympus, Lake Success, N.Y., U.S.A.). White light from a 75-W xenon arc lamp is collimated, passed through an excitation filter, reflected by a dichroic mirror, and focused onto the proximal end of the imaging fiber with a 10× or 20× microscope objective. Precise positioning of the imaging fiber surface with respect to the objective can be provided by a xy-micropositioner (Spindler and Hoyer, Milford, Mass. U.S.A.). Excitation light is transmitted from the fiber's proximal face to the distal face where it illuminates the fluorescently tagged molecules. The fluorescence light returning through the imaging fiber is collected by the microscope objective, transmitted through the dichroic mirror, filtered at an appropriate wavelength and detected by a charge couple device (CCD) camera (Philips Instruments, Slatersville, R.I., U.S.A.). The CCD camera is attached to a computer that possesses a video graphics card and image processing software such as, for example IP Lab (Signal Analytics, Vienna, Va. U.S.A.).

Other light sources which are useful in practicing the present invention include, but are not limited to, hydrogen or deuterium discharge lamps, incandescent filament lamps, mercury vapor lamps, xenon flash lamps and lasers such as optically pumped lasers, gas-discharge, pulsed gas lasers, chemical lasers, photodissociation lasers, gas-dynamic lasers, semiconductor lasers, etc. The wide variety of light sources of use with the present invention is offered by way of illustrating the flexibility of the individual components of an instrument of use with the invention. Numerous other useful variations in the components and the configuration of the above-described apparatus will be apparent to those of skill in the art.

Fluorescent-labeled molecules of use in practicing this aspect of the invention are known in the art. Exemplary fluorophores of use in the instant invention are displayed in Table 1, below. Other fluorophores of use in the present invention will be apparent to those of skill in the art.

A vast array of reactive derivatives of fluorophores appropriate for functionalizing biomolecules are commercially available (Molecular Probes, Eugene, Oreg., U.S.A.) or can be readily synthesized by those of skill in the art. Reactive groups which are present on biomolecules and can be derivatized with reactive fluorophores include, for example, amines, hydroxyl groups, sulfhydryl groups, histidine, urea, carboxylate, etc. For each of these functional groups, an array of reactions for their derivatives with probes or other reagents is available in the art. See, for example, Feeney, R. E., MODIFICATION OF PROTEINS, FOOD, NUTRITIONAL AND PHARMACOLOGICAL ASPECTS, Advances in Chemistry Series, Vol. 198, ACS, Washington, D.C., 1982, the disclosure of which is incorporated herein by reference.

TABLE 1

| FLUOROPHORES | EXCITATION WAVELENGTH | FLUORESCENCE EMISSION |
| --- | --- | --- |
| eosin | 520–530 nm | 530–580 nm |
| TRITC-amine | 555 nm | 570–610 nm |
| quinine | 330–352 | 382–450 |
| fluorescein W | 488–496 | 530 nm |
| acridine yellow | 464 nm | 500 nm |
| lissamine rhodamine | 567 nm | 580 nm |
| B sulfonyl chloride erythroscein | 504 nm | 560 nm |
| ruthenium (tris, bipyridinium) | 460 nm | 580 nm |
| Texas Red | 596 nm | 615 nm |
| nicotinamide adenine dinucleotide | 340 nm | 435 nm |
| flavin adenine dinucleotide | 450 nm | 530 nm |

In certain embodiments, the library is screened using methods other than fluorescence spectroscopy. For example, assays can be used to test the ability of a compound to interact with target binding sites or to inhibit the interaction of certain groups with binding the sites. In a preferred embodiment, assays which test the ability of the compound to interact with binding sites on a surface (e.g., panning assays) are used in screening libraries. Charych, D., et al., Chem. & Biol., 3:113–120 (1996).

In another exemplary embodiment, capillary electrophoresis (CE) can be used. CE is a convenient high resolution analytical technique requiring only femtomoles of material. CE allows separation of mixtures of molecules (ions, small molecules, polymers, proteins, micelles) on the basis of their charge and hydrodynamic drag. By adding library compounds to the buffer solution at varying concentration, and by monitoring the influence of the concentration of the library compound on the mobility of injected binding sites, it is possible to quantitate accurately the binding constant of the compound for the binding site. This technique is referred to as affinity capillary electrophoresis (ACE). For example, the affinity of a compound for a whole virus expressing binding sites can be determined using ACE. It has also been shown that ACE forms the basis of a very efficient library search. CE is also useful, as are gel permeation chromatography (GPC) and light scattering techniques.

Surface Plasmon Resonance Spectroscopy (SPR) can also be used to screen the array for the compound's ability to bind to a target surface. See, for example, Mrksich, M., et al., Langmair, p. 4383 (1995); Mrksich, M., et al., J. Am. Chem. Soc., 117:12009 (1995); Sigal, G. B., et al., Anal. Chem., 68:490 (1996).

Model Surfaces Based on Self-Assembled Monolayers (SAMs) can also be used to assay the subject library compounds. SAMs of alkanethiolates on gold and silver is another model system for studying adsorption, or other molecular events occurring at interfaces. See, e.g., Mrksich, M., et al., Ann. Rev. Biophys. Biomol. Struct., 25:55 (1996); Whitesides, G. M., et al., SELF-ASSEMBLED MONOLAYERS: MODELS FOR ORGANIC SURFACE CHEMISTRY, CRC Press, Boca Raton, 1995; Mrksich, M., et al., J. Am. Chem. Soc., 117:12009 (1995); Sigal, G. B., et al., Anal. Chem., 68:490 (1996); Lopez, et al., J. Am. Chem. Soc., 115:5877 (1993).

Inhibition assays can also be used, such as those which measure the extent to which a molecule prevents a biological surface (e.g., a virus) from binding to another biological surface (e.g., a cell). The molecule may bind competitively to the receptor, and prevent binding of the surface bound groups to the same binding site.

Another exemplary assay is the optical collision (OPTCOL) assay, and is based on the inhibition of attachment upon collision of one erythrocytes and one virus-coated microsphere in the presence of inhibitor. This assay is performed under an inverted microscope using parallel optical tweezers, with each of the tweezers holding one of the two colliding species. The OPTCOL assay allows quantitation of effectiveness of inhibitors that are active at <1 nM. Mammen, M. et al., Chem. Biol., 3:757–763 (1996).

Both the HAI and OPTCOL assays yield a concentration at which the inhibition is partially effective (i.e., a concentration at which approximately half the interactions between the compound and binding sites are inhibited). In the HAI assay, the inhibition constant is $K_{HA}$ or $K_{OPTCOL}$. When measuring inhibition constants whose values are reliably measurable using each assay, $K_{HA} \approx K_{OPTCOL}$. Both these inhibition constants can be referred to as $K_{INH}$.

A number of methods for probing, assessing and quantitating molecular interactions exist. Some assays are direct measures of affinity; from these affinities, one can extract free energies of interaction. Other assays measure a complex aggregate of characteristics, only one of which is free energy of interaction. These other characteristics may include extent of hydration, ability to stabilize a molecule or surface sterically and/or ability to crosslink multivalent receptors.

To quantify a binding constant thermodynamically (i.e., to obtain a binding constant), the relative proportions of uncomplexed and complexed group (or binding site) must be measured (directly or indirectly). Depending on the stability of the complex (related to its lifetime), different techniques can be used.

Aggregation assays can be used to measure the ability of a compound to aggregate a polyvalent binding site (precipitation, gel formation, aggregation). For example, a compound can precipitate polyvalent binding sites B on a surface in immunoprecipitation assays. Although the affinity of the entity is important in determining the ability of the compound to precipitate, other characteristics can be important. For example, at low concentrations, the compound may not bind to polyB; at some optimal concentration zone, precipitation occurs; while at higher concentrations, each binding site B is bound by a compound and precipitation again does not occur. In this example, which is analogous to antibody precipitation reactions, affinity alone does not determine the pattern of precipitation.

EXAMPLES

The following examples illustrate the use of the method of the present invention to initiate and control reactions which require the application of light, heat or a combination thereof. The reactions demonstrated in these examples include cycloadditions, cyclization to hydantoins of urea carbonyl derivatives, synthesis of thiazolidiones and the synthesis of 5,6-dihydropyrimidine-2,4-diones.

Example 1

This example illustrates a thermally allowed [4+2] cycloaddition reaction which occurs on the surface of an optical fiber. One of the components of the cycloaddition is tethered to the optical fiber via an amine group at the surface of the fiber.

As shown in Scheme 1, an optical fiber, the surface of which is derivatized with reactive primary amine groups, is reacted with maleic anhydride to form an optical fiber with a plurality of maleimide groups on its surface. The maleimide derivatized optical fiber is incubated with a solution of a dienopyranoside as heat is applied to the reaction via the optical fiber. The diene and maleimide groups couple to form a new six-membered ring with an endocyclic double bond.

Example 2

This example illustrates a photochemically mediated [2+2] cycloaddition reaction which occurs on the surface of an optical fiber.

As shown in Scheme 2, an optical fiber, the surface of which is derivatized with reactive primary amine groups, is reacted with acryloyl chloride. The resulting acrylamide derivatized optical fiber is suspended in an acetonitrile solution of a 3,4-dihydropyran analog. Nitrogen is continuously bubbled through the solution and the reaction mixture is irradiated by 350 nm light delivered through the optical fiber. The alkenes cyclize to provide a new four membered ring which is fully saturated.

In a variation of this reaction, the surface of the optical fiber is functionalized with reactive hydroxyl groups. The hydroxyl groups are derivatized with acryloyl chloride to provide an alkene tethered to the optical fiber. The alkene derivatized optical fiber is reacted with a second alkene which is in solution as is described above.

Example 3

This example demonstrates the formation of fused ring systems utilizing a series of [4+2] cycloadditions.

As shown in Scheme 3, an ether derivative which terminates in an alkene is tethered to the optical fiber. The optical fiber is immersed in a solution of a diene and heat is applied to the reaction mixture via the optical fiber. The reaction produces a new six-membered ring with an endocyclic double bond. Upon completion of this first reaction, the excess diene is washed away from the fiber and the fiber is suspended in a solution of a second diene. The second diene is either the same as the first diene or it is a different diene. Heat is again applied via the optical fiber and the tethered alkene and the free diene undergo cycloaddition to form a product with two fused six-membered rings. Again, the newly formed ring contains an endocyclic double bond. The steps of this reaction can be repeated multiple times with any number of different dienes.

Example 4

This example illustrates the synthesis of fused ring structures using a combination of photochemical [2+2] cycloadditions of alkenes and alkynes and [2+4] cycloadditions of alkenes and dienes.

Similar to Example 3, an alkene is tethered to the surface of the optical fiber as shown in Scheme 4. The derivatized optical fiber is immersed in a solution of an alkyne and the reaction mixture is irradiated via the optical fiber. The reaction produces a cyclobutene analog. Following completion of the reaction, the optical fiber is washed to free it of any remaining alkyne. The optical fiber is immersed in a solution of a diene and heat is transferred to the reaction mixture via the optical fiber. The product comprises a cyclobutane ring which is fused to a cyclohexene ring. Because of the presence of the double bond in the cyclohexene ring of the reaction product, the product can act as a constituent in a further cycloaddition. When an alkene is utilized, the product contains a cyclobutane fused to a cyclohexane which is fused to a cyclobutene. Alternatively, another diene can be added to form a fused ring system having two adjacent six-membered rings. This process is repeated with different solution-phase constituents until the desired product results.

Example 5

This example illustrates the use of the methods and apparatus of the present invention to produce new compounds by [2+2] intramolecular photocycloaddition reactions of compounds tethered to the optical fiber.

As shown in Scheme 5, a cyclohexenone olefin derivative is tethered to an optical fiber via an imine linkage formed between a primary amine group on the fiber and the ketone moiety of the cyclohexenone ring. The derivatized optical fiber is immersed in purified hexene and light of approximately 330 nm is passed through the optical fiber for approximately one hour. The resulting product is a fused ring system comprising a six-membered ring, a four-membered ring and a five-membered ring.

Example 6

This example demonstrates the synthesis of hydantoins using the methods and apparatus of the present invention.

An optical fiber which is functionalized with available reactive hydroxyl groups is derivatized with an amino acid. The amino acid is linked to the fiber via an ester linkage formed between the carboxylic acid group of the amino acid and the hydroxyl group of the fiber. While heat is supplied to the reaction via the optical fiber, the tethered amino acid is treated with an acyl azide to form the corresponding substituted urea. The urea is cyclized to the hydantoin by immersing the optical fiber in an aqueous acid and heating the urea via the optical fiber. The cyclization step also leads to the cleavage of the hydantoin from the optical fiber.

Example 7

Example 7 illustrates the synthesis of 4-thiazolidinones, compounds which interact with G-protein coupled receptors, using the methods and apparatus of the invention to supply heat to the reacting species.

X = O, NH

In a variation of this method, the optical fiber is functionalized with reactive hydroxyl groups and the amino acid is tethered to the fiber by an ester linkage. The other reaction steps are substantially as described previously.

Example 8

This example demonstrates the synthesis of 5,6-dihydropyrimidine-2,4-diones, a class of herbicidal agents, using the methods and apparatus of the present invention.

An optical fiber which is derivatized with active hydroxyl groups is derivatized with acryloyl chloride to produce an acrylic ester. A primary amine is added to the double bond of this ester. While heat is supplied by the fiber, the amine group is reacted with an acyl azide to produce the corresponding urea. The pyrimidine ring is closed and the compound is cleaved from the fiber by treatment with aqueous acid at approximately 95° C.

The above examples illustrate only a few of the many reaction types which can be practiced within the scope of the present invention. Within each of the many reaction types there exists a multiplicity of individual chemical components which can be transformed into a combinatorial library of compounds with desirable properties. The activities of the compounds of the library can reside anywhere within a broad spectrum of different activity types and activity strengths. Library compounds can have activities which are pharmaceutical, pesticidal, herbicidal, etc. Once the library of compounds is assembled, it can be screened for activity by any one of a number of techniques. Particularly desirable, in the context of the present invention, is the ability to screen the activity of the compounds while they are bound to the optical fiber. A host of spectroscopic techniques, including fluorescence, infrared, ultraviolet, visible and raman spectroscopies can be used to study the compounds of the newly synthesized libraries.

All publications, patents and patent applications mentioned in this specification are incorporated herein by reference to the same extent as if each individual publication, patent or patent application was specifically and individually indicated to be incorporated herein by reference.

Although the foregoing invention has been described in some detail by way of illustration and example for purposes of clarity and understanding, it will be obvious that certain changes and modifications can be practiced within the scope of the appended claims.

What is claimed:

1. A method of making an array of compounds on a substrate, said substrate comprising at least a first region and a second region, wherein each of said regions comprises an optical fiber having a reactive group covalently bound thereto, said method comprising:
    (a) covalently attaching a first component to said reactive group on said optical fiber of said first region, forming a first immobilized component;
    (b) covalently attaching a first component to said immobilized reactive group on said optical fiber of said second region, forming a second immobilized component;
    (c) delivering a second component to said first immobilized component;
    (d) delivering via said optical fiber of said first region an amount of light sufficient to form a covalent bond between said first immobilized component and said second component delivered to said first immobilized component, thereby forming a first compound immobilized on said optical fiber of said first region;
    (e) delivering a second component to said second immobilized component; and
    (f) delivering via said optical fiber of said second region an amount of light sufficient to form a covalent bond between said second immobilized component and said second component delivered to said second immobilized component, thereby forming a first compound immobilized on said optical fiber of said second region.

2. The method in accordance with claim 1 wherein said reactive group on said optical fiber of said first region is a member selected from the group consisting of carboxyls, hydroxyls, haloalkyls, dienophiles, aldehydes, ketones, sulfonyl halides, thiols, amines, sulfhydryls, alkenes and epoxides.

3. The method in accordance with claim 1 wherein said first component is covalently attached to said reactive group on said optical fiber of said first region through a stable bond.

4. The method in accordance with claim 1 wherein said first component is covalently attached to said reactive group on said optical fiber of said first region through a cleavable bond.

5. The method in accordance with claim 1 wherein said first component is covalently attached to said reactive group on said optical fiber of said first region through a spacer group wherein said spacer group forms a first linkage with said reactive group and a second linkage with said first component.

6. The method in accordance with claim 5 wherein said first linkage and said second linkage are different.

7. The method in accordance with claim 5 wherein said spacer group comprises a hydrolyzable linkage.

8. The method in accordance with claim 7 wherein said hydrolyzable linkage is between said first linkage and said second linkage.

9. The method in accordance with claim 5 wherein said spacer group comprises a cleavable linkage.

10. The method in accordance with claim 9 wherein said cleavable linkage is between said first linkage and said second linkage.

11. The method in accordance with claim 1 wherein said first immobilized component and said second immobilized component are the same.

12. The method in accordance with claim 1 wherein said second component delivered to said first immobilized component and said second component delivered to said second immobilized component are the same.

13. The method in accordance with claim 1 wherein step (c) occurs substantially simultaneously with step (d).

14. The method in accordance with claim 1 wherein step (e) occurs substantially simultaneously with step (f).

15. The method in accordance with claim 1 wherein said first immobilized component and said second immobilized component are independently selected and are dieneophiles.

16. The method in accordance with claim 1 wherein said second component delivered to said first immobilized component and said second component delivered to said second immobilized component are independently selected and are dienes.

17. The method in accordance with claim 1 wherein said optical fiber of said first region is constructed of a material selected from the group consisting of glass, quartz and plastic.

18. The method in accordance with claim 1 wherein said first region comprises at least 10 optical fibers.

19. The method in accordance with claim 1 wherein said first region comprises at least 50 optical fibers.

20. The method in accordance with claim 1 wherein said first region comprises at least 100 optical fibers.

21. The method in accordance with claim 1 wherein said first region comprises at least 1,000 optical fibers.

22. The method in accordance with claim 1 wherein at least 10 different compounds are made.

23. The method in accordance with claim 1 wherein at least 50 different compounds are made.

24. The method in accordance with claim 1 wherein at least 100 different compounds are made.

25. The method in accordance with claim 1 wherein at least 1,000 different compounds are made.

26. The method in accordance with claim 1 wherein at least 10,000 different compounds are made.

27. The method in accordance with claim 1, further comprising the steps of:
(g) delivering a third component to said first compound immobilized on said optical fiber of said first region; and
(h) delivering via said optical fiber of said first region an amount of light sufficient to form a covalent bond between said first compound immobilized on said optical fiber of said first region and said third component delivered to said first compound immobilized on said optical fiber of said first region, thereby forming a compound immobilized on said optical fiber of said first region consisting of the reaction product of said first compound immobilized on the first region of the array and the third component.

28. The method in accordance with claim 1, further comprising the steps of:
(g) delivering a third component to said first compound immobilized on said optical fiber of said second region; and
(h) delivering via said optical fiber of said second region an amount of light sufficient to form a covalent bond between said first compound immobilized on said optical fiber of said second region and said third component delivered to said first compound immobilized on said optical fiber of said second region, thereby forming a compound immobilized on said optical fiber of said second region consisting of the reaction product of said first compound immobilized on the second region of the array and the third component.

29. The method in accordance with claim 1, further comprising the steps of:
(g) delivering a third component to said first compound immobilized on said optical fiber of said first region;
(h) delivering via said optical fiber of said first region an amount of light sufficient to form a covalent bond between said first compound immobilized on said optical fiber of said first region and said third component delivered to said first compound immobilized on said optical fiber of said first region, thereby forming a compound immobilized on said optical fiber of said first region consisting of the reaction product of said first compound immobilized on the first region of the array and the third component;
(i) delivering a third component to said first compound on said optical fiber of said second region; and
(j) delivering via said optical fiber of said second region an amount of light sufficient to form a covalent bond between said first compound immobilized on said optical fiber of said second region and said third component delivered to said first compound immobilized on said optical fiber of said second region, thereby forming a compound immobilized on said optical fiber of said second region consisting of the reaction product of said first compound immobilized on the second region of the array and the third component.

30. The method in accordance with claim 1, wherein a member selected from said covalent bond formed in step (d), said covalent bond formed in step (f) and combinations thereof are formed by thermal reactions, photochemical reactions and combinations thereof.

31. A method of making an array of compounds on a substrate, said substrate comprising at least a first region and a second region, wherein each of said regions comprises an optical fiber having a reactive group covalently bound thereto, said method comprising:
(a) covalently attaching a first component to said reactive group on said optical fiber of said first region, forming a first immobilized component;
(b) covalently attaching a first component to said reactive group on said second region, forming a second immobilized component;
(c) delivering via said optical fiber of said first region an amount of light sufficient to intramolecularly rearrange said first immobilized component, thereby forming a first compound immobilized on said optical fiber of said first region; and
(d) delivering via said optical fiber of said second region an amount of light sufficient to intramolecularly rearrange said second immobilized component, thereby forming a first compound immobilized on said optical fiber of said second region.

32. The method in accordance with claim 31 wherein said reactive group on said optical fiber of said first region is a member selected from the group consisting of carboxyls, hydroxyls, haloalkyls, dienophiles, aldehydes, ketones, sulfonyl halides, thiols, amines, sulfhydryls, alkenes and epoxides.

33. The method in accordance with claim 31 wherein said first component is covalently attached to said reactive group on said optical fiber of said first region through a spacer group.

34. The method in accordance with claim 31 wherein said first component attached to said reactive group on said optical fiber of said first region and said second component attached to said reactive group on said optical fiber of said second region are independently selected and are alkenes.

35. The method in accordance with claim 31, wherein a member selected from the intramolecular rearrangement of step (c), the intramolecular arrangement of step (d) and combinations thereof are formed by thermal reactions, photochemical reactions and combinations thereof.

36. A method of making an array of compounds on a substrate, said substrate comprising at least two regions, wherein each of said regions comprise an optical fiber having an unprotected reactive group covalently attached thereto, said method comprising:
(a) covalently attaching a first component to said unprotected reactive group on said optical fiber of said first region, forming a first immobilized component;
(b) covalently attaching a first component to said unprotected reactive group on said second region, forming a second immobilized component;
(c) delivering a second component to said first immobilized component;
(d) delivering via said optical fiber of said first region an amount of light sufficient to form a covalent bond between said first immobilized component and said second component delivered to said first immobilized component, thereby forming a first compound immobilized on said optical fiber of said first region;
(e) delivering a second component to said second immobilized component; and
(f) delivering via said optical fiber of said second region an amount of light sufficient to form a covalent bond between said second immobilized component and said second component delivered to said second immobilized component, thereby forming a first compound immobilized on said optical fiber of said second region.

37. A method of making an array of compounds on a substrate, said substrate comprising at least a first region and a second region, wherein each of said regions comprises an optical fiber having a spacer arm covalently attached thereto, said spacer arm comprising an unprotected reactive group, said method comprising:

(a) covalently attaching a first component to said unprotected reactive group of said spacer arm of said first region, forming a first immobilized component;

(b) covalently attaching a first component to said unprotected reactive group of said spacer arm of said second region, forming a second immobilized component;

(c) delivering a second component to said first immobilized component;

(d) delivering via said optical fiber of said first region an amount of light sufficient to form a covalent bond between said first immobilized component and said second component delivered to said first immobilized component, thereby forming a first compound immobilized on said optical fiber of said first region;

(e) delivering a second component to said second immobilized component; and (f) delivering via said optical fiber of said second region an amount of light sufficient to form a covalent bond between said second immobilized component and said second component delivered to said second immobilized component, thereby forming a first compound immobilized on said optical fiber of said second region.

* * * * *